(12) United States Patent
Heisler

(10) Patent No.: US 7,666,200 B2
(45) Date of Patent: Feb. 23, 2010

(54) ENDOSCOPIC CUTTING INSTRUMENT WITH AXIAL AND ROTARY MOTION

(75) Inventor: Gary R. Heisler, Middletown, CT (US)

(73) Assignee: Target Medical Innovations LLC, St. Pete Beach, FL (US)

( * ) Notice: Subject to any disclaimer, the term of this patent is extended or adjusted under 35 U.S.C. 154(b) by 119 days.

(21) Appl. No.: 11/634,102

(22) Filed: Dec. 6, 2006

(65) Prior Publication Data

US 2008/0021487 A1    Jan. 24, 2008

Related U.S. Application Data

(60) Provisional application No. 60/831,986, filed on Jul. 19, 2006.

(51) Int. Cl.
*A61B 17/32* (2006.01)

(52) U.S. Cl. ......................... 606/171; 606/180

(58) Field of Classification Search .............. 606/127, 606/159, 161, 167–171, 177–179, 79–82, 606/84; 600/36, 564; 408/17; 83/647

See application file for complete search history.

(56) References Cited

U.S. PATENT DOCUMENTS

| | | | | |
|---|---|---|---|---|
| 4,603,694 A * | 8/1986 | Wheeler | ........................ | 606/171 |
| 4,749,376 A * | 6/1988 | Kensey et al. | ................... | 604/22 |
| 4,850,354 A * | 7/1989 | McGurk-Burleson et al. | ............. | 606/170 |
| 5,217,479 A | 6/1993 | Shuler | ......................... | 606/180 |
| 5,226,910 A | 7/1993 | Kajiyama et al. | ............ | 606/171 |
| 5,269,798 A | 12/1993 | Winkler | ......................... | 606/170 |
| 5,364,395 A * | 11/1994 | West, Jr. | ........................ | 606/46 |
| 5,527,331 A * | 6/1996 | Kresch et al. | ................ | 606/170 |
| 5,601,583 A * | 2/1997 | Donahue et al. | ............. | 606/170 |
| 5,665,101 A * | 9/1997 | Becker et al. | ................ | 606/180 |
| 5,669,926 A * | 9/1997 | Aust et al. | ..................... | 606/170 |
| 5,693,063 A | 12/1997 | Van Wyk et al. | ............. | 606/167 |
| 5,709,698 A * | 1/1998 | Adams et al. | ................ | 606/180 |
| 5,741,287 A * | 4/1998 | Alden et al. | ................. | 606/170 |
| 5,766,199 A | 6/1998 | Heisler et al. | ................ | 606/180 |
| 5,810,860 A * | 9/1998 | Adrian | ......................... | 606/169 |
| 5,843,106 A | 12/1998 | Heisler | ........................ | 606/167 |
| 5,868,767 A * | 2/1999 | Farley et al. | ................. | 606/159 |
| 6,001,116 A * | 12/1999 | Heisler et al. | ................ | 606/180 |
| 6,053,928 A | 4/2000 | Van Wyk et al. | ............. | 606/167 |
| 6,217,598 B1 * | 4/2001 | Berman et al. | ............... | 606/167 |
| 6,419,684 B1 | 7/2002 | Heisler et al. | ................ | 606/170 |
| 6,447,525 B2 | 9/2002 | Follmer et al. | .............. | 606/159 |
| 6,527,736 B1 * | 3/2003 | Attinger et al. | ............... | 604/43 |
| 2001/0005778 A1 * | 6/2001 | Ouchi | ......................... | 600/564 |
| 2003/0083684 A1 * | 5/2003 | Cesarini et al. | ............. | 606/170 |
| 2004/0049217 A1 * | 3/2004 | Ross et al. | ................... | 606/171 |
| 2004/0059363 A1 * | 3/2004 | Alvarez et al. | .............. | 606/170 |
| 2004/0267157 A1 * | 12/2004 | Miller et al. | ................. | 600/565 |
| 2005/0065538 A1 * | 3/2005 | Van Wyk | ..................... | 606/159 |
| 2007/0282361 A1 * | 12/2007 | Da Rold et al. | ............. | 606/171 |

* cited by examiner

*Primary Examiner*—Anhtuan T Nguyen
*Assistant Examiner*—Elizabeth Houston
(74) *Attorney, Agent, or Firm*—Chalin A. Smith; Smith Patent Consulting, LLC

(57) ABSTRACT

Disclosed herein is an endoscopic surgical assembly having improved cutting efficiency. In particular, the present invention provides an endoscopic shaver assembly configured for automated axial as well as rotational motion so as to enhance tissue resection.

22 Claims, 7 Drawing Sheets

ENDOSCOPIC CUTTING INSTRUMENT WITH AXIAL AND ROTARY MOTION

PRIORITY

This application claims the benefit of U.S. Provisional Application Ser. No. 60/831,986 filed Jul. 19, 2006, the contents of which are incorporated by reference herein in its entirety.

TECHNICAL FIELD OF THE INVENTION

The present invention relates generally to the field of endoscopic tissue resection and powered surgical instruments for use therein. More particularly, the invention relates to a minimally invasive endoscopic cutting instrument having an elongated inner member axially slidable and rotatably situated within an elongated stationary outer member, both inner and outer members having, at their distal ends, cutting apertures which cooperate to resect tissue during endoscopic surgical procedures.

BACKGROUND OF THE INVENTION

In contrast to conventional surgery, which requires a relatively large incision in order to gain access to a surgical site within a body, endoscopic procedures utilize natural passages, or, alternatively, involve the formation of very small portals to gain access to the surgical site of interest. Accordingly, an endoscopic procedure is often referred to as minimally invasive surgery. One advantage of performing endoscopic surgery is that since the portions of the body that are cut are reduced, the portions of the body that need to heal after the surgery are likewise reduced. Still another advantage of endoscopic surgery is that it exposes less of the interior tissue of the body to the open environment. This minimal opening of the body lessens the extent to which its internal tissue and organs are open to infection.

Advancements in this field of "closed" surgery, such as arthroscopy and, more generally, endoscopic surgery, have led to the creation of numerous minimally invasive surgical cutting instruments. As noted above, in closed surgery, access to the surgical site is gained via one or more portals. As such, the instruments used in the surgical procedure must be sufficiently smooth and elongated to permit the distal ends of the instruments to reach the surgical site with minimal trauma to neighboring tissues. One end of the instrument, often referred to as the "distal end", is designed to be positioned at the surgical site. The opposed end of the instrument, often referred to as the "proximal end", extends out of the patient's body. The distal end of the instrument is typically provided with some type of working head designed to manipulate the tissue against which it is placed whereas the proximal end of the instrument is provided with a mechanism for the user to remotely control the working head.

Surgical cutting instruments for use in closed surgery—often referred as endoscopic "shavers"—are typically composed of a pair of concentrically disposed, close-ended, generally tubular members, more typically an elongated outer tubular member terminating in a distal opening or "cutting window", an aperture situated in the distal end, on the distal end side wall, or both, and an elongated inner tubular member, slidably and concentrically disposed in the outer tubular member, whose distal end is disposed adjacent the cutting window of the outer tubular member. The distal end of the inner tubular member typically has a surface or edge for engaging tissue via the distal opening in the outer tubular member and cooperates with the opening to shear, cut or trim tissue, a process often referred to as "resection". For example, the inner tubular member may be rotatably driven about its axis from its proximal end by a handpiece having a small electric motor which is controlled by one or more finger actuated switches on the handpiece, one or more foot switches on a console supplying power to the handpiece, or some other analogous control means. Cut tissue can then be aspirated through the hollow lumen of the inner tubular member to be collected via a vacuum tube communicating with the handpiece. The distal end of the inner tubular member can be provided with a number of dimensions or configurations, depending upon the surgical procedure to be performed. Similarly, the opening in the distal end of the outer tubular member may be adapted to cooperate with the particular configuration of the distal end of the inner tubular member. For example, the inner and outer tubular members can be configured to produce side cutting or end cutting, or a combination of the two, to cut soft or bony tissues or combinations thereof. These various configurations are generally referred to in the art as "shaver blades".

The cutting windows of a shaver each have perimeters composed of two relatively longitudinal, straight or curvilinear edges connected at their proximal and distal ends by two relatively transverse edges. The configuration of the longitudinal edges, and to a lesser extent the transverse edges is determined by the intended use of the shaver. For instance, shavers intended for use on soft tissue will be provided with cutting windows configured for increased resection efficiency but relatively low resistance to deformation since the cutting forces are typically low. Conversely, those shavers intended for use on tough tissue, such as meniscus or vertebral discs, will be provided with a greater resistance to deformation since the cutting forces are quite high.

Resection of tissue by a shaver blade is typically accomplished by the cooperative interaction between the sharp beveled edges of the inner and outer cutting windows. As the inner and outer windows come into alignment, vacuum within the lumen of the inner member aspirates tissue into the opening formed. Continued rotation of the inner member causes the inner cutting edges to approach the outer cutting edges. Tissue in the cutting window between the inner and outer edges is either trapped between the edges or ejected from the window. Tissue trapped between the edges is either cut by the edges as they approach each other or torn by the cutting edges as they pass and rotate away from each other. The resected tissue is then aspirated from the site through the inner lumen of the inner member.

Resection efficiency can be improved by decreasing the relative portion of the material that is ejected from the window, and increasing the portion that is trapped between the edges and resected. Decreasing the relative portion ejected from the window can be achieved through the use of sharper cutting edges. Illustrative means for increasing the sharpness of the cutting edge include decreasing the included angle of the cutting edge, decreasing the edge radius, and decreasing the roughness of the surfaces over which tissue must slide during resection. For example, U.S. Pat. No. 5,843,106 (Heisler) discloses a shaver with increased resection efficiency produced by an outer cutting window configuration having "sharpened" low included-angle cutting edges. The relative portion of tissue ejected from the window during closure may also be decreased by adding teeth to either the inner cutting edges or outer cutting edges or both. Shavers having inner cutting edges with teeth are described in the art, for example in U.S. Pat. No. 5,217,479 (Shuler) and U.S. Pat. No. 5,269,798 (Winkler), each of which disclose shavers having inner cutting edges with teeth, such teeth being formed by a "through-cutting" process, such as wire electrical discharge machining (wire EDM), or by grinding. Teeth so formed are efficient at retaining tissue within the window so that it can be cut by the low included angle outer cutting edges as the inner and outer edges converge. The inner cutting edges do little cutting since the teeth form a very large included angle cutting edge.

The Cuda™ by Linvatec Corporation (Largo, Fla.) and the Tomcat™ by Stryker Corporation (Kalamazoo, Mich.) each have teeth on both the inner and outer cutting edges, the edges being formed by a two-dimensional, through-cutting process such as grinding or wire EDM. The edges formed have large included angles, a geometry that is inefficient for cutting tissue. Shavers having these two-dimensionally shaped teeth on the inner and outer cutting edges separate tissue principally by tearing as the edges pass each other when the cutting window is closed. Such tearing is undesirable since the torn tissue frequently becomes trapped in the gap between the inner and outer tubular members, thereby causing clogging. This problem is specifically addressed in U.S. Pat. No. 6,053, 928 (Van Wyk et al.), which discloses a shaver having a plurality of teeth on the laterally opposed cutting edges of an outer window, the cutting edges being symmetrical when viewed in a plane normal to the axis of the tube. The cutting edges are formed so that, when viewed in any such plane, the edges have low included angles, in the valleys between the teeth as well as the teeth. The Great White™ shaver by Linvatec, constructed in accordance with the principles of the '928 patent, is very efficient at resecting tissue and experiences reduced clogging due to the sharpness of the outer cutting edges.

When a shaver is used with a constant rotation imparted to the inner member, tissue in close proximity to the window is sucked into the window and either resected or ejected from the window in the manner previously herein described. Tissue which is ejected from the window, or the remaining tissue adjacent to a resected portion, is swept in the direction of the rotation. When the cutting window is opened again by the rotation of the inner member, the amount of tissue which will be pulled into the window by vacuum in the inner lumen is diminished from that of the previous opening event because of this directional "set" of the tissue. That is, because the tissue is already preferentially oriented in the direction of the rotation of the approaching inner cutting edge, it is difficult for that inner cutting edge to get sufficient "bite" to retain the tissue in the cutting window for resection. Because of this, arthroscopic shavers are generally used in an "oscillate" mode when cutting tissue. In this mode the inner is rotated in one direction for a predetermined number of revolutions, whereupon its rotation is reversed for the same predetermined number of revolutions. The inner cutting edges approach the tissue from alternating directions thereby greatly increasing the relative portion of tissue that is sucked into the window and is resected rather than ejected.

As noted above, a conventional shaver blade assembly is composed of a stationary outer assembly and an inner assembly. The inner assembly is typically composed of a generally tubular member with a closed distal end and a proximal-end hub configured for removable coupling a drive mechanism of a powered handpiece so as to transmit rotational motion from the handpiece to the distal end of the inner assembly. The outer assembly is typically composed of a generally tubular member with a closed distal end and a proximal hub means for removably mounting the shaver blade assembly in a powered handpiece. An elastic member transmits an axial force distally on the inner assembly so that contact is maintained between the outer surface of the distal end of the inner member and the inner surface of the distal end of the outer member, the surfaces together functioning as a bearing. In some shaver systems, the elastic member is a spring affixed to the hub of the inner assembly. In other systems, the elastic member is a spring in the handpiece in which the shaver is mounted. The distal bearing surfaces are spherical on most (almost all) shavers, although shavers with other shapes are produced for specialized purposes. The radius of the spherical inner surface of the outer member is slightly larger than that of the spherical external surface of the inner member. The application of the axial force to the inner member by the elastic member creates quite high Herzian contact stresses at the bearing surfaces. Since shavers are used with rotational speeds as high as 5,000 rpm, chafing or galling of these surfaces is frequently a problem. To prevent galling, the materials of the inner and outer distal ends are carefully selected and the components hardened and machined to very precise shapes, frequently with form tolerances of as little 0.0002 inches. The surface finishes of the bearing surfaces are also critical since irregularities in the surfaces can lead to high localized stresses which result in galling of the surfaces during use. Galling of the bearing surfaces during use creates metallic debris which can be deposited into the surgical site, with negative consequences to the patient. In severe cases, galling may cause welding of the inner and outer members so as to make the shaver unusable. As a result, some manufacturers coat the inner member bearing surface with a gall-resistant metallic material, while others make the distal end of the inner member from a gall resistant alloy. In any event, galling and metallic debris created by shaver blades is still a frequent problem since inspection of the inner surface of the outer member is very difficult and minor manufacturing abnormalities can create surfaces which are not to specification.

Closely related to arthroscopic shavers are a category of devices known in the art as arthroscopic burs, which are used for resecting bone. Burs differ from shavers in that the inner member has multiple cutting edges arranged on a rotating element (the bur head), with cutting achieved solely by the inner cutting edges. While shavers cut by cooperative interaction of the inner and outer cutting edges, burs cut with the inner edges only. Also, shavers use a vacuum to draw tissue into a cutting window for resection while burs use suction only to remove debris from the surgical field. Burrs are ineffective for cutting soft tissue. Examples of commercially available burrs include, but are not limited to, the Spherical Burr, Oval Burr, Cyclone Burr, and Vortex Router by Conmed Corporation (Utica, N.Y.).

The Helicut™ burr by Smith and Nephew Incorporated (Andover, Mass.), and the Lightning™ by Conmed Corporation are specialty burrs which cut both soft tissue and bone. The instruments have a helical rotational inner member with two cutting edges, and an open-ended outer member with edges which cooperatively resect soft tissue with the edges of the inner member. The resected tissue is removed from the site by the action of the helical inner as well as by a vacuum applied to the proximal end of the outer member. The Helicut and Lightning are unique in that they resect both bone and soft tissue, and does not have a tubular inner member. Because the outer tube does not have a closed end, there is no bearing surface at the distal end, the bearing surface being between the inner and outer hubs at the proximal end of the device.

Thus, there are a number of commercially available embodiments of endoscopic cutting instruments. Nevertheless, despite the above described improvements, there remains a clear need in the art to increase the efficiency of endoscopic cutting instruments and shaver blades. The present invention is directed to such a need.

SUMMARY OF THE INVENTION

In view of the foregoing, it is a primary object of the present invention to provide an endoscopic shaver assembly having improved cutting efficiency. To that end, the present invention provides increased relative motion between the cutting edges so as to cut tissue more readily. Specifically, the present invention combines automated relative axial movement with rotational motion so as to enhance tissue resection.

It is, accordingly, an object of this invention to provide an endoscopic shaver assembly with high resection efficiency due to axial as well as rotational motion between the cutting edges.

It is also an object of this invention to provide a method for producing axial as well as rotational motion in the inner cutting edges of an endoscopic shaver assembly without requiring modification to the handpiece.

It is a further object of this invention to provide a method for increased resection efficiency in an endoscopic, more particularly arthroscopic, shaver blade assembly using a combination of axial and rotational motion.

Accordingly, it is an object of the present invention to provide an endoscopic surgical assembly composed of an elongated inner member and an elongated outer members, each of the elongated members having a coordinating hub disposed at its proximal end, one or more apertures disposed at its distal end, and a central lumen extending along its length and defining inner and outer surfaces, the inner member sized so as to be slidably received within the lumen of the outer member such that when the inner and outer hubs are connected, the apertures of the inner and outer members cooperate to resect tissue in contact therewith, the assembly further including a means for automatically transmitting relative axial movement between the inner and outer members when said inner member and outer member are relatively rotated.

It is a further object of the present invention to provide the endoscopic surgical assembly with an elastic member that maintains contact between the outer surface of the distal end of the inner member and the inner surface of the distal end of the outer member when the inner and outer hubs are connected. Examples of such members include coiled springs and the like.

In a preferred embodiment, the inner and outer members comprise concentric, closed-ended tubes provided with laterally disposed cooperating cutting windows. However, the assembly may also be fabricated with an open-ended tubular outer member and a helical inner member provided with one or more cutting elements.

In a preferred embodiment, each cutting window is provided with a perimeter comprised of two longitudinal cutting edges and two transverse cutting edges. The cutting edges may be linear, curvilinear or a combination thereof, thereby providing the cutting window with an overall shape that is regular or irregular, symmetrical or asymmetrical shape. Examples of suitable cutting window shapes include, but are not limited to, circles, ellipses, polygons such as rectangles, squares, rhomboids, trapezoids, and the like, as well as combinations thereof.

While the present invention is not limited to cutting windows of any particular size, shape and dimension, in order to achieve efficient cutting, it is preferable that at least a portion of one or more cutting edges is angled or beveled so as to yield a sharp cutting surface. A suitable included angle for the beveled cutting edges preferably ranges from 15 to 70 degrees, and more preferably ranges between 20 and 50 degrees.

It is yet a further object of the present invention, to provide cooperating elements that automatically transmit relative axial movement between the inner and outer members when said inner member and outer member are relatively rotated, in particular cooperating elements disposed within said inner and outer hubs. Examples of such cooperating elements include, but are not limited to, mating cams and cam followers, screw threads, worm gears, worm wheels, pneumatic devices, hydraulic mechanisms, magnetic assemblies, and push-pull connectors.

Another object of the present invention is to provide a method for resecting a target tissue within a surgical site of interest comprising the steps of:

(a) introducing endoscopic surgical assembly of the present invention into a surgical site of interest;

(b) rotating the inner member relative to the outer member, wherein rotation of the inner member a sufficient distance results in the automatic axial movement of the inner member relative to the outer member, further wherein the relative axial and rotational movement of the members results in relative axial and rotational movement of their respective apertures which cooperate to cut the target tissue.

The method of the present invention may further include the optional steps of (a) rotating the inner member relative to the outer tubular member in one direction for a first predetermined number of revolutions then rotating the inner member relative to the outer tubular member in an opposite direction for a second predetermined number of revolutions (a process known in the art as "oscillating" the assembly" or (b) applying suction to one or more of the inner and outer members so as to draw target tissue in contact with one or more cutting elements and aspirate resected tissue from the surgical site.

These and other objects are accomplished in the invention herein described, directed to an improved shaver blade wherein the inner and outer cutting edges are subjected to axial as well as rotational relative motion. Further objects and features of the invention will become more fully apparent when the following detailed description is read in conjunction with the accompanying figures and examples. However, it is to be understood that both the foregoing summary of the invention and the following detailed description are of a preferred embodiment, and not restrictive of the invention or other alternate embodiments of the invention. In particular, while the invention is described herein with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims.

For example, although the figures and examples are directed to a two-lobed cam and cam follower, it is readily apparent that the number of cam elements is not a critical feature of the invention. Accordingly, the cam may be single or multi-lobed, composed of one, two, three, four, five, up to ten lobes as needed. Likewise, although the figures and examples describe axial motion imparted by cam action, the invention is not limited thereto. As noted above, several other means for transmitting relative axial movement between the inner and outer members are contemplated herein. For example, in addition to cams and cam followers, automated axial displacement may be provided by mating screw threads, worm gears, worm wheels, pneumatic devices, hydraulic mechanisms, magnetic assemblies, push-pull connectors and the like.

In addition, although the figures and examples describe axial motion imparted by means disposed between the inner assembly hub and the outer assembly hub, it is readily apparent that the means for transmitting relative axial movement between the inner and outer members can be positioned anywhere along the length of the device, from the proximal hub end to the distal cutting end. In addition, in an alternate embodiment, the axial motion can be provided by the handpiece into which the shaver blade assembly is mounted.

DETAILED DESCRIPTION OF THE PREFERRED EMBODIMENTS

Figure 1:
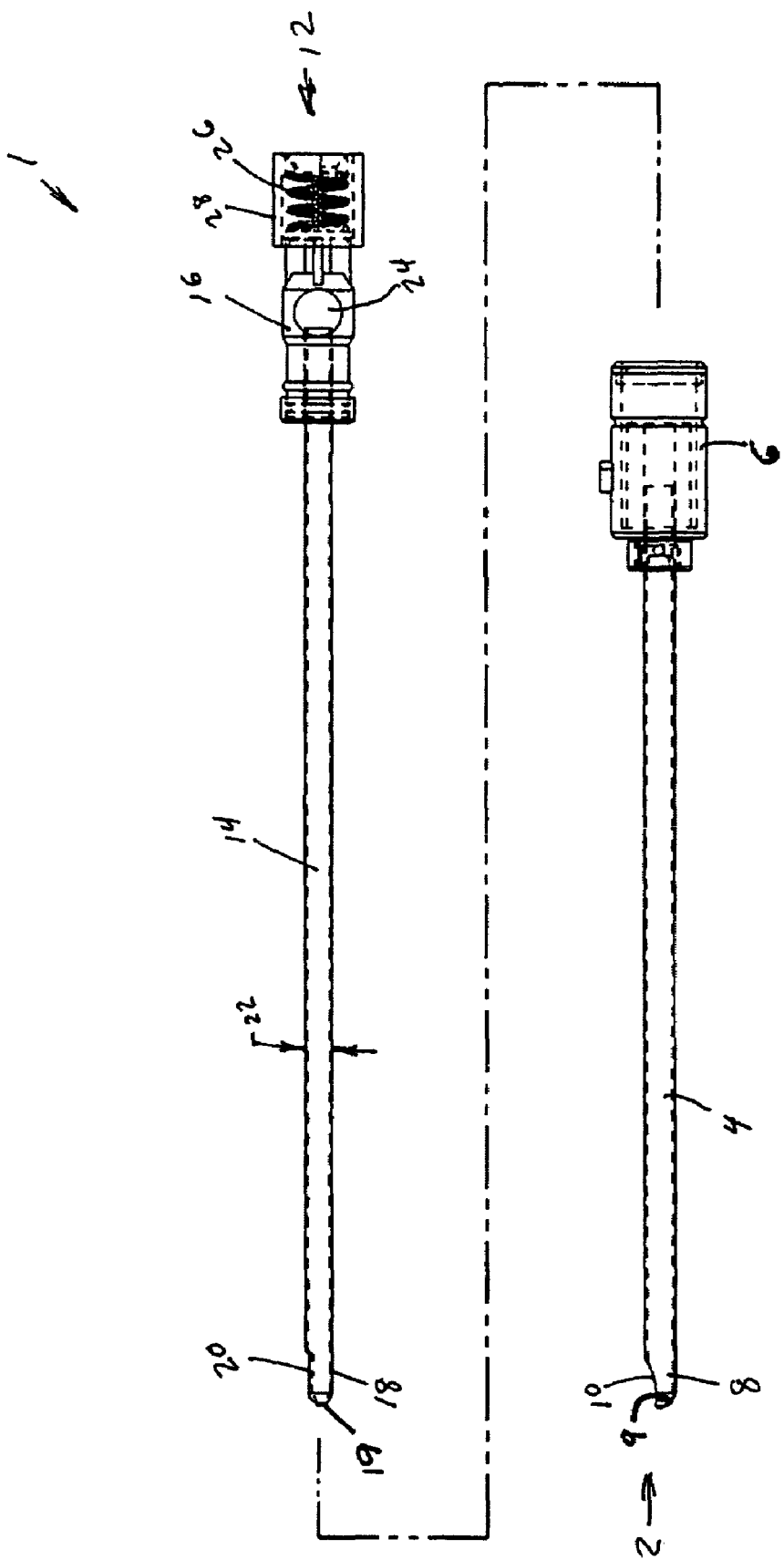
FIG. 1 is a disassembled view of a prior art arthroscopic shaver blade assembly.
Figure 2:
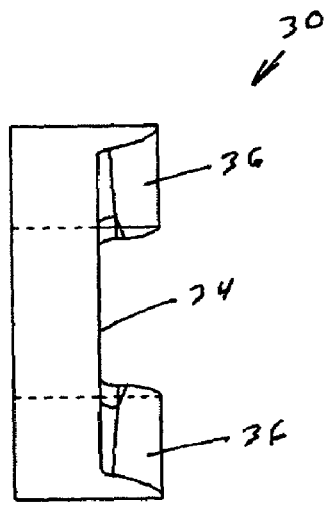
FIG. 2 is a plan view of a cam for a shaver constructed in accordance with the principles of this invention.
Figure 5:
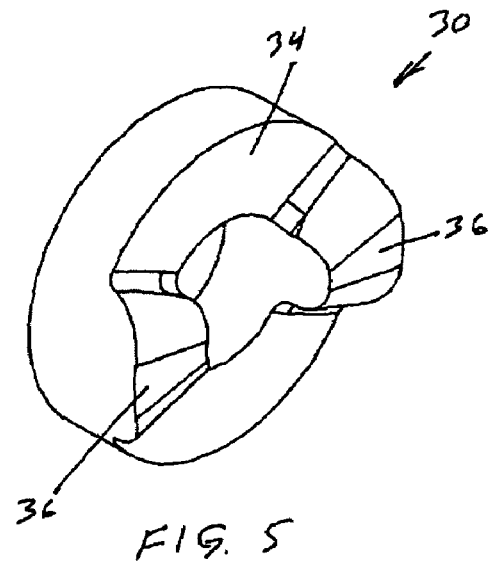
FIG. 5 is a perspective view of the object of FIG. 2.
Figure 3:
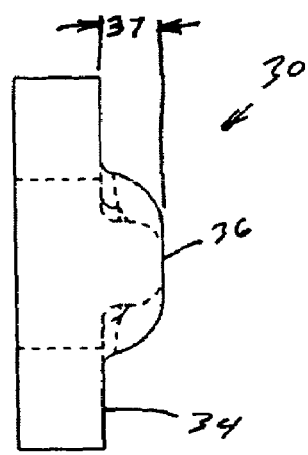
FIG. 3 is a side elevational view of the object of FIG. 2.
Figure 4:
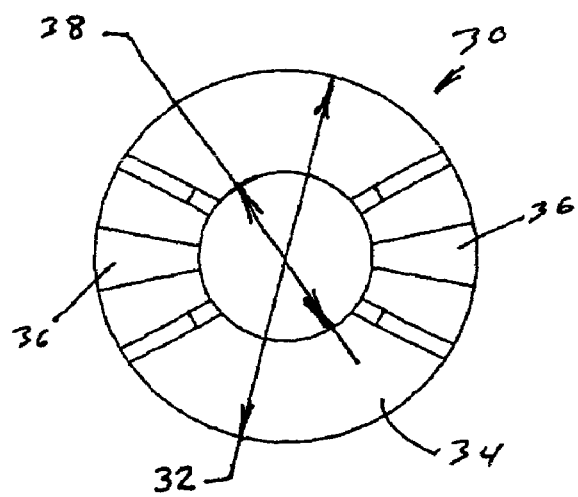
FIG. 4 is a distal axial view of the object of FIG. 2.

Although any methods and materials similar or equivalent to those described herein can be used in the practice or testing of embodiments of the present invention, the preferred methods, devices, and materials are now described. However, before the present materials and methods are described, it is to be understood that this invention is not limited to the particular sizes, shapes, dimensions, materials, methodologies, protocols, etc. described herein, as these may vary in accordance with routine experimentation and optimization. It is also to be understood that the terminology used in the description is for the purpose of describing the particular versions or embodiments only, and is not intended to limit the scope of the present invention which will be limited only by the appended claims.

Unless otherwise defined, all technical and scientific terms used herein have the same meaning as commonly understood by one of ordinary skill in the art to which this invention belongs. However, in case of conflict, the present specification, including definitions, will control.

In the context of the present invention, the following definitions apply:

The words "a", "an" and "the" as used herein mean "at least one" unless otherwise specifically indicated. Thus, for example, reference to a "cam lobe" is a reference to one or more cams and equivalents thereof known to those skilled in the art, and so forth.

The term "proximal" as used herein refers to that end or portion which is situated closest to the user of the device, farthest away from the target surgical site. In the context of the present invention, the proximal end of the inventive device includes the handpiece region.

The term "distal" as used herein refers to that end or portion situated farthest away from the user of the device, closest to the target surgical site. In the context of the present invention, the distal end of the inventive device includes the respective cutting windows of the inner and outer tubular members.

The term "rotational" as used herein refers to the revolutionary movement about the center point or longitudinal axis of the device. In the context of the present invention, rotation of the elongated inner tubular member relative to the elongated outer tubular member, which typically is held in a stationary position, results in relative rotation of their respective cutting apertures which coordinate to resect target tissue within the surgical site of interest.

The term "axial" as used herein refers to the direction relating to or parallel with the longitudinal axis of the device. In the context of the present invention, the addition of relative axial movement between the elongated outer tubular member and the elongated inner tubular member slidably received therein results in improved cutting efficiency.

The instant invention has both human medical and veterinary applications. Accordingly, the terms "subject" and "patient" are used interchangeably herein to refer to the person or animal being treated or examined. Exemplary animals include house pets, farm animals, and zoo animals. In a preferred embodiment, the subject is a mammal.

Hereinafter, the present invention is described in more detail by reference to the Figures and Examples. However, the following materials, methods, figures, and examples only illustrate aspects of the invention and are in no way intended to limit the scope of the present invention. As such, methods and materials similar or equivalent to those described herein can be used in the practice or testing of the present invention.

FIG. 1 depicts a conventional prior art arthroscopic shaver 1 comprised of an elongated tubular outer assembly 2, typically formed from a metallic material, having a distal portion 4 and a proximal portion 6 forming a hub suitable for mounting in a shaver handpiece. Distal portion 4 has a distal end 8 in which is formed cutting window 10 and spherical inner distal surface 19. Shaver 1 also includes an elongated tubular inner assembly 12, also of metal, having a distal portion 14 and a proximal portion 16 forming a hub suitable for transmitting rotational motion provided by a handpiece to inner assembly 12. Distal portion 14 has a distal end 18 in which is formed cutting window 20 and a distal spherical surface 19. Diameter 22 of distal portion 14 of inner assembly 12 is slightly less than the diameter of the inner lumen of distal portion 4 of outer assembly 2 such that that inner assembly 12 may be rotatably positioned therein for use. Spring 26 disposed within spring retainer 28 when shaver 1 is mounted in a suitable powered handpiece creates a distal axial force on inner assembly 12 so as to maintain axial contact between distal spherical portion 19 of inner assembly 12 and the inner surface 9 of distal end 8 of outer assembly 2.

During use, distal portion 14 of inner assembly 12 is rotated within distal portion 14 of outer assembly 4 in an oscillatory manner, that is, the inner tube is rotated in one direction a predetermined number of revolutions, stopped, and then rotated in the opposite direction a predetermined number of revolutions. This action is repeated as long as the handpiece in which the shaver is mounted is activated. Suction supplied to the lumen of distal portion 14 of outer assembly 12, via passage 24 in communication therewith, draws tissue into contact with, and partially into, the opening formed by angular alignment of windows 10 and 20. Continued rotation of inner assembly 12 causes tissue to be cut by the cooperative action of the cutting edges of windows 10 and 20.

Additional information on shaver construction and operation may be found in U.S. Pat. No. 5,693,063 (Van Wyk et al.), U.S. Pat. No. 5,766,199 (Heisler et al.), and U.S. Pat. No. 5,843,106 (Heisler), the contents of which are incorporated by reference herein in their entirety.

Referring now to FIGS. 2 through 5, cam 30 of outer diameter 32 has a first axial surface 34 having raised portions 36, and an inner diameter 38. Raised portions 36 are displaced axially distance 37 from surface 34 and have a predetermined contour.

Figure 6:
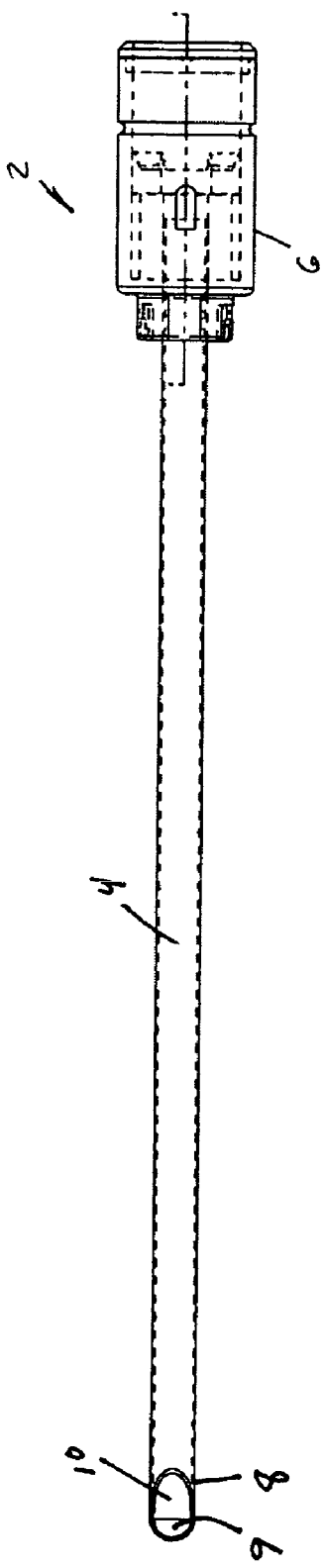
FIG. 6 is a plan view of the outer assembly of a shaver constructed in accordance with the principles of this invention.
Figure 7:
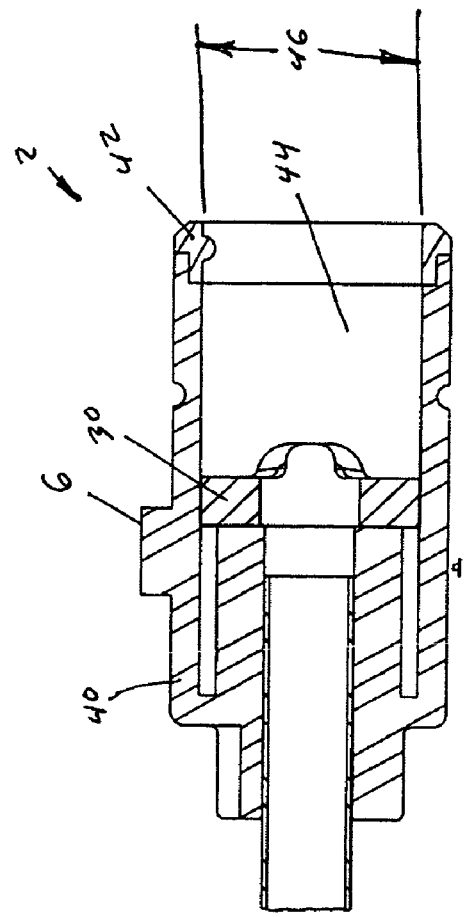
FIG. 7 is an expanded side elevational sectional view of the proximal portion of the object of FIG. 6.
Figure 11:
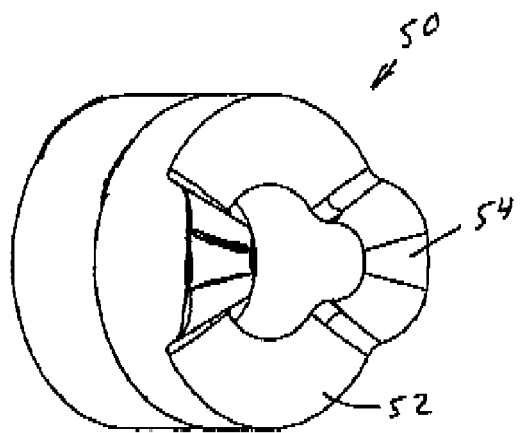
FIG. 11 is a perspective view of the object of FIG. 8.
Figure 8:
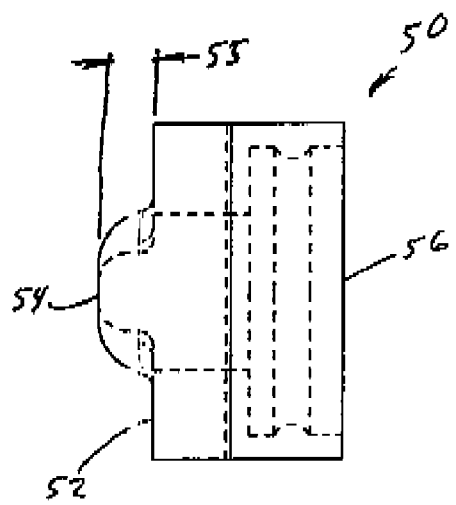
FIG. 8 is a plan view of a cam follower of a shaver constructed in accordance with the principles of this invention.
Figure 10:
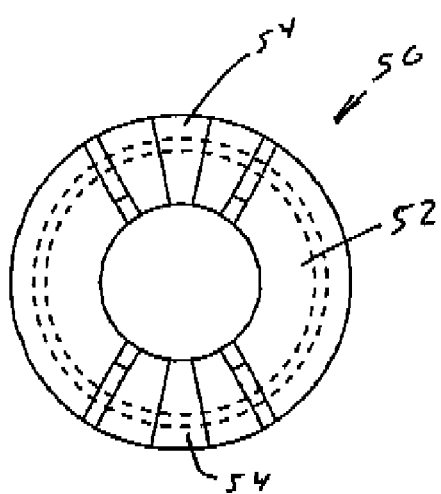
FIG. 10 is a proximal axial view of the object of FIG. 8.
Figure 9:
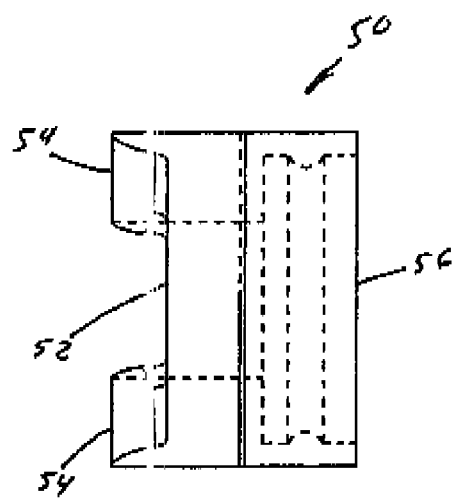
FIG. 9 is a side elevational view of the object of FIG. 8.

Referring now to FIGS. 6 and 7, outer assembly 2 of an endoscopic shaver formed in accordance with the principles of this invention has a proximal hub assembly 6 having a hub 40 and retainer 42, analogous in construction to those of prior art shaver 1. However, the hub assembly 2 of the instant invention further includes cam element 30, coaxial with outer assembly 2, cam 30 being compressibly retained within cylindrical recess 44, the diameter 32 of cam 30 being slightly larger than diameter 46 of recess 44.

As seen in FIGS. 8 through 11, cam follower element 50 has a first axial surface 52 with raised portions 54, and a second axial surface 56 having a pocket formed therein, the pocket being configured to allow connection of cam follower 50 to an inner hub. Raised portions 54 are axially displaced a distance 55 from surface 52. Distance 55 is less than or equal to distance 37 of cam 30.

Figure 12:
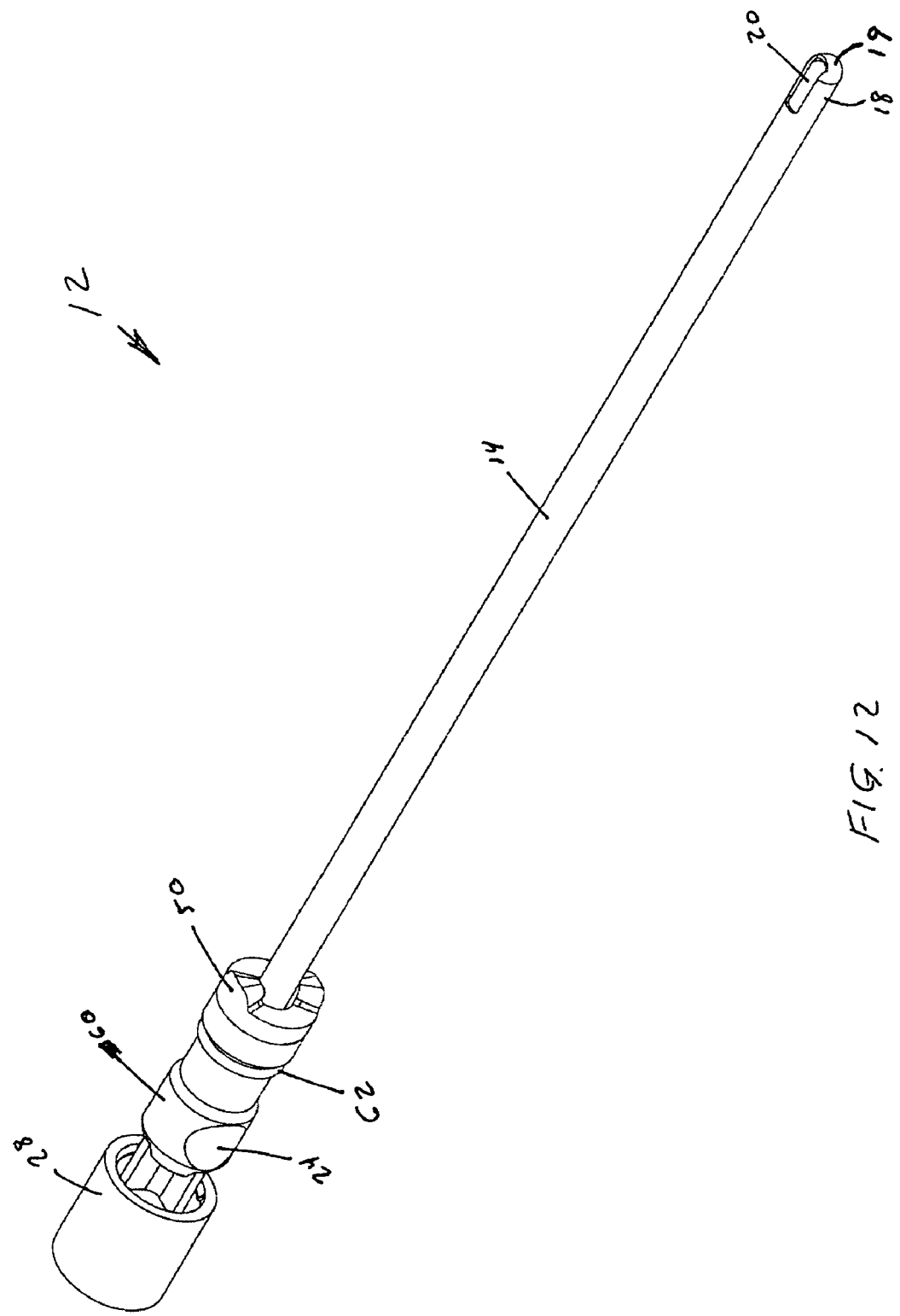
FIG. 12 is a perspective view of the inner assembly of a shaver constructed in accordance with the principles of this invention.

FIG. 12 depicts the inner assembly 12 of a shaver formed in accordance with the principles of this invention, wherein cam follower 50 is assembled to distal end 62 of inner hub 60.

Figure 13:
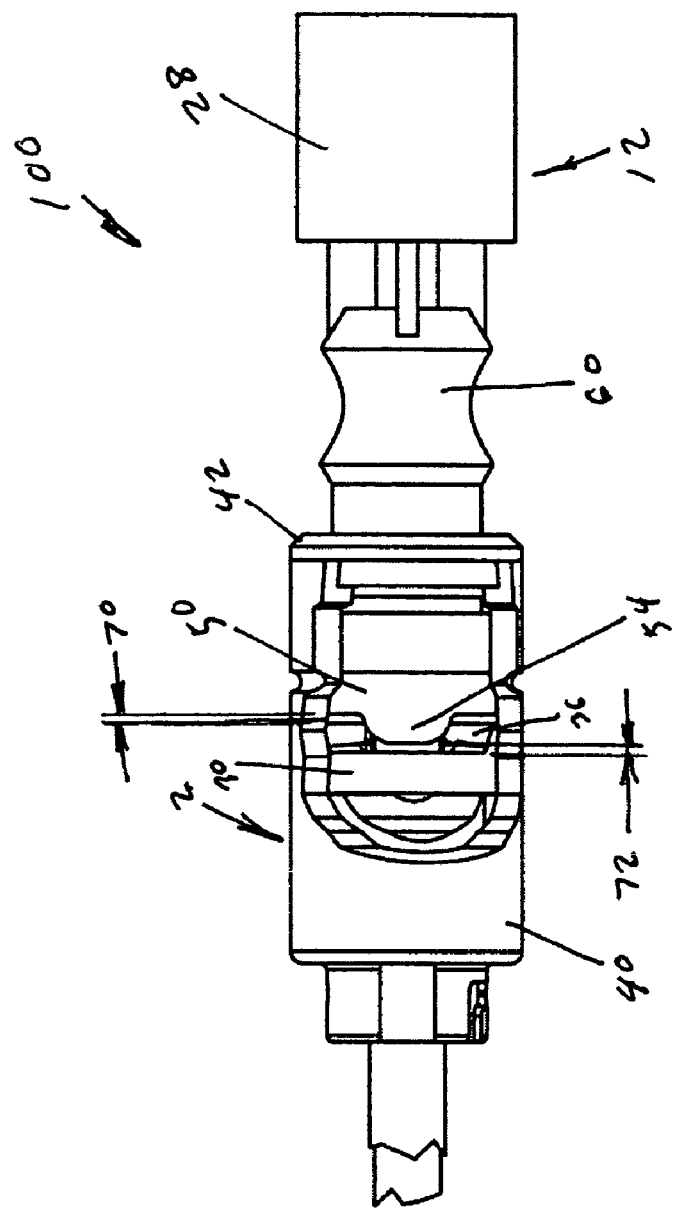
FIG. 13 is an expanded plan view of a shaver constructed in accordance with the principles of this invention with the inner assembly in a first position relative to the outer assembly.
Figure 13:
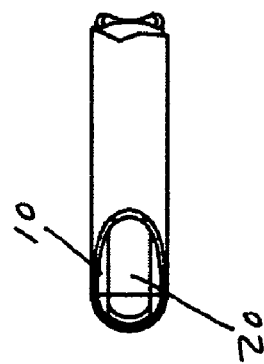
Figure 14:
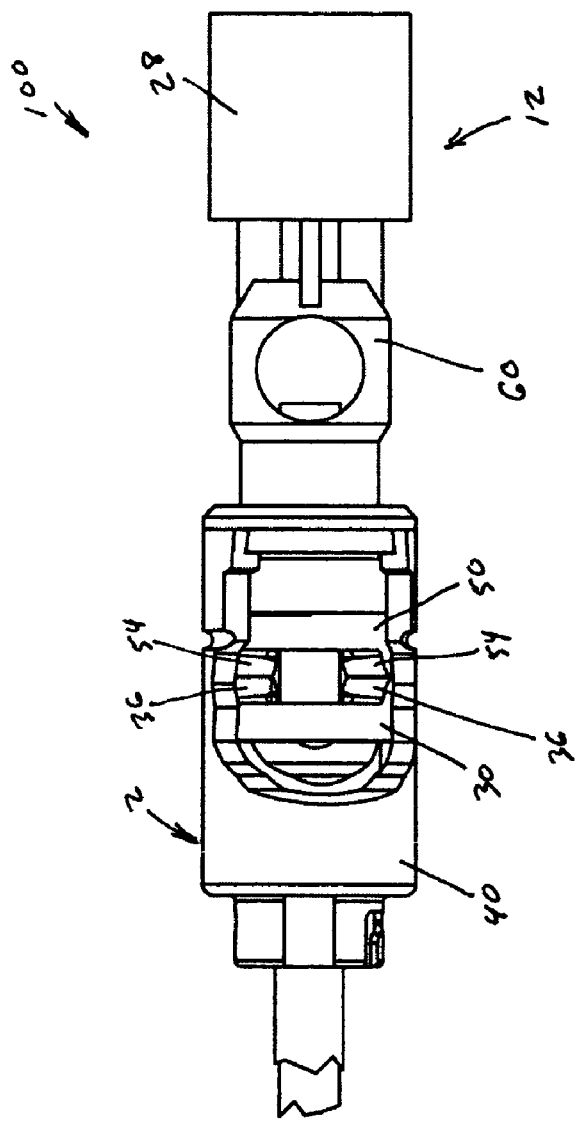
FIG. 14 is an expanded plan view of the objects of FIG. 13 with the inner assembly in a second position relative to the outer assembly.
Figure 14:
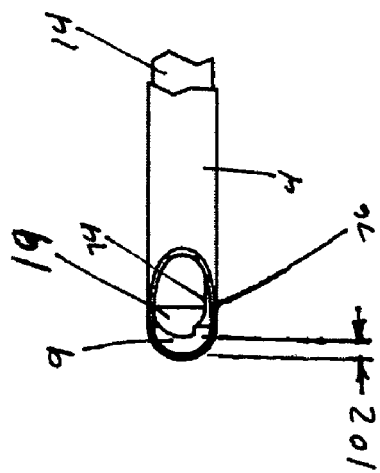

FIG. 13 depicts a shaver 100 constructed in accordance with the principles of this invention, wherein the inner assembly 12 is in a first angular position relative to outer assembly 2. In this first position, cutting window 20 of inner assembly 12 is aligned with window 10 of outer assembly 2. Distal outer spherical surface 19 of tubular element 14 of inner assembly 12 (see FIG. 1) is in contact with inner spherical surface 9 of tubular element 4 of outer assembly 2. Cam 30 is not in contact with cam follower 50. Raised portions 36 of cam 30 are axially separated from surfaces 52 of cam 50 distance 70. Raised portions of 54 of follower 50 are axially separated from surfaces 34 of cam 30 by distance 72. Distances 70 and 72 are approximately equal. In other embodiments, distance 70 is greater than 72. In still other embodiments distance 72 is greater than distance 70. FIG. 14 depicts a shaver 100 constructed in accordance with the principles of this invention, wherein the inner assembly 12 is in a second angular position relative to outer assembly 2. In this second position, cutting window 20 of inner assembly 12 is rotated so that the edge 74 of window 20 is in close proximity to and approaching edge 76 of outer window 10 as when resecting tissue therebetween. Raised portions 54 of cam follower 50 are in contact with raised portions 36 of cam 30. Distal end spherical surface 19 of distal portion 14 of inner assembly 12 is displaced axially distance 102 from the inner surface 9 of distal end 8 of elongated portion 4 of outer assembly 2. Spring 26 in combination with spring retainer 28 in coordination with the handpiece maintain contact between the surfaces of cam 30 and follower 50. Distance 102 is preferably between 0.005 and 0.16 inches, and more preferably between 0.01 and 0.12 inches.

In use, as inner assembly 12 is rotated within outer assembly 2 between a first position, shown in FIG. 13, and a second position, shown in FIG. 14. In this manner, inner assembly 12 undergoes both rotational and axial motion. This results in an axial relative motion between the inner and outer cutting edges as the edges approach each other. This, in turn, results in increased resection efficiency.

The increase in efficiency is readily understood by considering a knife cutting a steak. Simply pushing the knife edge vertically into the steak will cut the steak; however, much greater force is required than that required if the steak knife is "sawed" back and forth while the vertical force is applied. When a cutting edge is forced into tissue in a simple, direct motion without relative motion parallel to the cutting edge, the tissue is separated by a force perpendicular to the cutting edge due to the wedge shape of the cutting edge. The separating stress in the tissue caused by the wedge must exceed the strength of the material. The friction force of the tissue against the knife blade tends to prevent the separation of the tissue. In contrast, when the cutting edge moved parallel to the cutting edge (i.e., a sawing motion") the tissue at the cutting edge sees a separating force caused by the wedge shape of the cutting edge, and also a tearing force caused by friction between the moving cutting edge and the tissue at the edge. If a motion is imparted to the cutting edge parallel to the cutting edge, friction between the edge and the tissue aids the cutting process. This is in contrast with cutting in which such motion is not present and friction between the edge and the tissue hinders the cutting process.

In the same manner, a shaver blade constructed in accordance with the principles of this invention has an axial relative motion which causes increased resection efficiency by more effectively separating tissue in contact with the cutting edges.

The invention herein disclosed also increases the efficiency of shavers which have teeth on the inner cutting edges, outer cutting edges or both. In a preferred embodiment previously herein described, the cutting edges are straight or curvilinear. However, it will be readily understood that a number of different cutting window profiles may be used. For example, the longitudinal portions and distal tip edges of the inner and/or outer cutting edges may have contours including, but not limited to, one or more teeth, ridges, waves, pyramidal shapes and the like. The forms of these contours may be optimized for increased resection efficiency when the cutting edges are subjected to axial motion.

The contours of cam 30 and cam follower 50 may be optimized for improved performance. For instance, the angular width of raised portions 36 and 54 respectively can be optimized such that the axial motion of the inner cutting edges occurs when the inner and outer cutting edges are approaching each other and in close proximity. Also, the contour of the transitions to and from the raised portions can be optimized so that the axial motion occurs at an optimal rate and axial acceleration is minimized so that spring 26 is able to maintain contact between the cam and follower.

In the embodiment previously herein described, bearing surfaces 9 and 19 of inner assemblies 2 and 12 respectively, are in contact except when raised portions 36 of cam 30 (FIGS. 2 through 4) and raised portions 54 (FIGS. 9 through 11) are in contact. In other embodiments, cam 30 and follower 40 are in contact throughout the cycle so as to act as irregular bearing surfaces, surfaces 9 and 19 not being in contact throughout the cycle. Because surfaces 9 and 19 are not in contact, it is not necessary that they be formed to the tight tolerances and high-quality surface finishes required for bearing surfaces. Because of this, embodiments in which the cam and follower act as bearing surfaces may be produced at reduced cost compared to shavers in which surfaces 9 and 19 are bearing surfaces.

The invention herein described, endoscopic instruments which cut tissue through the cooperative interaction of inner and outer cutting edges through combined rotational and axial motion, also encompasses instruments having inner members which are not tubular. A cam and follower acting as the bearing surfaces for such device increases their efficiency in the same manner as the embodiments previously herein described.

Shavers constructed in accordance with the principles of this invention may be used in existing handpieces without modification to the handpieces, the resilient member of the shaver system allowing for the axial motion of the inner assembly. In the preferred embodiment previously described, spring 26 and spring retainer 28 remain a part of the inner assembly 12. In other embodiments, the spring and spring retainer are part of the handpiece into which shaver 100 is inserted.

In the preferred embodiment previously described, spring 26 and spring retainer 28 are part of inner assembly 12. In other embodiments the spring and spring retainer are part of the handpiece into which shaver 100 is inserted.

In a preferred embodiment, the relative axial motion is provided by a coordinating cam and cam follower. While the examples described herein describe assembly of the cam to the inner tubular member and cam follow to the outer tubular member, it will be readily understood that these elements may be reversed without affecting the overall operation of the device. In addition, as noted above, the present invention contemplates other means for providing the relative motion axial as well as rotational motion, for example through use with a specially configured handpiece adapted for such movement. When a cam and follower are used to provide the axial motion, the resulting motion is synchronized with the rotation of the inner assembly. In embodiments in which the motion is provided by the handpiece, the motion may be synchronized with the rotational motion, or independent of the rotational motion. When the motion is not synchronized with the shaver rotation, the axial motion repetition frequency is preferably between 10 and 5,000 cycles per second, and more preferably between 20 and 1,000 cycles per second.

It is also anticipated that shavers for soft tissue produced in accordance with the principles of this invention will cut with a high efficiency when operated with a constant rotational motion. This will allow their use in low-cost handpieces in which only constant rotational motion is supplied. In yet another embodiment the shaver is integral with a low-cost handpiece so that the device is a limited re-use disposable item.

The concepts of the invention herein disclosed may be applied to any conventional shaver which has linear as well as rotational motion regardless of the means by which the axial motion is generated.

The invention may also be advantageously applied to endoscopic burs used for contouring bone. Axial motion supplied to the bur during use increases the resection efficiency and produces a smoother surface.

The disclosure of each publication, patent or patent application mentioned in this specification is specifically incorporated by reference herein in its entirety. However, nothing herein is to be construed as an admission that the invention is not entitled to antedate such disclosure by virtue of prior invention.

The invention has been illustrated by reference to specific examples and preferred embodiments. However, it should be understood that the invention is intended not to be limited by the foregoing description, but to be defined by the appended claims and their equivalents.

What is claimed:

1. An endoscopic surgical assembly comprising an elongated inner member and an elongated outer member, each of said elongated members comprising a concentric, closed-ended tube provided with a coordinating hub disposed at its proximal end, a laterally facing aperture disposed at its distal end, and a central lumen extending along its length and defining inner and outer surfaces, said inner member sized so as to be slidably received within the lumen of said outer member such that said when said inner and outer hubs are connected, the distal outer surface of the inner member contacts the distal inner surface of the outer member to form a bearing surface and the respective laterally facing apertures of said inner and outer members, each of which is provided with at least one longitudinal cutting surface, cooperate to resect tissue in contact therewith, said assembly further comprising a means for automatically transmitting relative back and forth axial movement between said inner and outer members when said inner member and outer member are relatively rotated in an oscillatory fashion, in one direction for a first predetermined number of revolutions then in an opposite direction for a second predetermined number of revolutions.

2. The assembly of claim 1, further comprising an elastic member that transmits an axial force distally on the inner member to maintain contact between the outer surface of the distal end of the inner member and the inner surface of the distal end of the outer member when said inner and outer hubs are connected.

3. The assembly of claim 1, wherein said elastic member comprises a coiled spring affixed to the inner hub.

4. The assembly of claim 1, wherein each of said cutting windows has a perimeter comprised of two longitudinal cutting edges and two transverse cutting edges.

5. The assembly of claim 4, wherein one or more of said cutting edges are beveled.

6. The assembly of claim 5, wherein one or more of said beveled culling edges are provided with plurality of teeth.

7. The assembly of claim 6, wherein the angle of said beveled cutting edges ranges from 15 to 70 degrees.

8. The assembly of claim 1, wherein said means for automatically transmitting relative axial movement between said inner and outer members when said inner member and outer member are relatively rotated comprises cooperating elements disposed along said inner and outer members.

9. The assembly of claim 8, wherein said cooperating elements are disposed within said inner and outer hubs.

10. The assembly of claim 8, wherein said cooperating elements comprise a cam disposed on the distal end of said inner member hub and a mating cam follower disposed on the proximal end of said outer member hub.

11. The assembly of claim 10, wherein said cam is integral with the distal end of said inner member hub and said mating cam follower is integral with said outer member hub.

12. The assembly of claim 10, wherein said cam comprises a separate annular ring having one or more raised lobes or protuberances on its distal facing surface, said ring being slidably disposed about the periphery of said elongated inner member and positioned against the distal end of said inner member hub.

13. The assembly of claim 10, wherein said mating cam follower comprises a compressible disc having one or more raised projections on its proximal facing surface, said disc retained within a cylindrical recess provided on the proximal end of the outer member hub.

14. The assembly of claim 8, wherein cooperating elements comprise a cam disposed on the proximal end of said outer hub and a mating cam follower disposed on the distal end of said inner hub.

15. The assembly of claim 14, wherein said cam and cam follower are provided with a plurality of interacting lobes or projections.

16. The assembly of claim 8, wherein said cooperating elements comprise a cam and mating cam follower disposed within a handpiece upon which the shaver assembly is mounted.

17. The assembly of claim 1, wherein the relative back and forth axial movement is on the order of 0.005 to 0.16 inches.

18. The assembly of claim 1, wherein the relative back and forth axial movement is on the order of 0.01 to 0.12 inches.

19. The assembly of claim 1, wherein said means for automatically transmitting relative axial movement between said inner and outer members when said inner member and outer member are relatively rotated is capable of an axial repetition frequency up to 5,000 cycles per second.

20. A method for resecting a target tissue within a surgical site of interest comprising the steps of:

(a) introducing the device of claim 1 into the surgical site;
(b) rotating the inner member relative to the outer member, wherein rotation of the inner member a sufficient distance results in the automatic axial movement of the inner member relative to the outer member, further wherein the relative axial and rotational movement of the members results in relative axial and rotational movement of their respective apertures which cooperate to cut the target tissue.

21. The method of claim 20, further comprising the step of rotating said inner member relative to said outer tubular member in one direction for a first predetermined number of revolutions then rotating said inner member relative to said outer tubular member in an opposite direction for a second predetermined number of revolutions.

22. The method of claim 20, wherein said inner and outer members comprise concentric, closed-ended tubes provided with laterally disposed cooperating cutting windows, further comprising the step of applying suction to the proximal end of the surgical assembly so as to draw target tissue into contact with the cooperating cutting windows and aspirate resected tissue from the surgical site through the central lumen of said inner tubular member.

* * * * *